(12) United States Patent
Babson et al.

(10) Patent No.: US 12,268,366 B2
(45) Date of Patent: Apr. 8, 2025

(54) INCREASING BATTERY LIFE IN HANDHELD DEVICE

(71) Applicant: Welch Allyn, Inc., Skaneateles Falls, NY (US)

(72) Inventors: David Matthew Babson, Warners, NY (US); Kenneth V. Coon, III, Jordan, NY (US); James Stuart Ledwith, Syracuse, NY (US); Jeffrey K. Moat, Ithaca, NY (US); David Gregory Perkins, Tully, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 304 days.

(21) Appl. No.: 17/723,967

(22) Filed: Apr. 19, 2022

(65) Prior Publication Data

US 2022/0330789 A1    Oct. 20, 2022

Related U.S. Application Data

(60) Provisional application No. 63/176,863, filed on Apr. 19, 2021.

(51) Int. Cl.
*A61B 1/06* (2006.01)
*A61B 1/00* (2006.01)
*A61B 1/227* (2006.01)

(52) U.S. Cl.
CPC .......... *A61B 1/227* (2013.01); *A61B 1/00032* (2013.01); *A61B 1/00036* (2013.01); *A61B 1/00066* (2013.01); *A61B 1/0684* (2013.01)

(58) Field of Classification Search
CPC ........... A61B 1/00006; A61B 1/00025; A61B 1/00027; A61B 1/00029; A61B 1/00032; A61B 1/00034; A61B 1/00036; A61B 1/06; A61B 1/0655; A61B 1/061; A61B 1/0684; A61B 1/227; A61B 1/2275; A61B 3/0008; A61B 3/12; A61B 5/0077; A61B 3/00; H05B 45/50; H05B 47/20
See application file for complete search history.

(56) References Cited

U.S. PATENT DOCUMENTS

| 7,871,407 | B2  | 1/2011  | Howell |
| 8,109,981 | B2* | 2/2012  | Gertner ............... A61N 5/0603 607/92 |
| 9,393,078 | B2  | 7/2016  | Shibahara et al. |
| 9,526,481 | B2  | 12/2016 | Storz et al. |

(Continued)

FOREIGN PATENT DOCUMENTS

| JP | 2018181574 A | * 11/2018 |
| WO | WO2007026158 A1 | 3/2007 |

OTHER PUBLICATIONS

English translation of JP 2018181574 (2024).*

(Continued)

*Primary Examiner* — Julianna N Harvey
*Assistant Examiner* — Anna V. Little
(74) *Attorney, Agent, or Firm* — Lee & Hayes, P.C.

(57) ABSTRACT

Systems and methods may determine an amount of current being drawn by a light source and determine, based on the amount of current, a type of light source. Based on the type of light source, an amount of time associated with disabling the light source may be determined. A voltage may be supplied to the light source for the amount of time.

18 Claims, 5 Drawing Sheets

(56) References Cited

U.S. PATENT DOCUMENTS

| 10,058,247 B2 | 8/2018 | Sagalovich et al. |
| 10,278,681 B2 | 5/2019 | Wood et al. |
| 2009/0187077 A1 | 7/2009 | Hosoda et al. |
| 2013/0096539 A1* | 4/2013 | Wood ................ H02J 7/00047 606/1 |
| 2014/0012078 A1* | 1/2014 | Coussa ............... A61B 1/0655 600/117 |
| 2014/0135581 A1 | 5/2014 | Wikstroem Shemer et al. |
| 2018/0102230 A1* | 4/2018 | Shen .................. A61B 1/00029 |
| 2019/0037669 A1* | 1/2019 | Hieb ...................... H05B 47/20 |
| 2019/0216307 A1* | 7/2019 | Coon ................ A61B 1/00124 |

OTHER PUBLICATIONS

Chinese First Office Action mailed Jul. 12, 2022 for Chinese Patent Application No. 202220895988.2, a foreign counterpart to U.S. Appl. No. 17/723,967, 5 pages.
Chinese Office Action mailed Oct. 31, 2023 for Chinese Patent Application No. 202320502531.5, a foreign counterpart to U.S. Appl. No. 17/723,967, 4 pages.
Chinese Office Action mailed Mar. 26, 2024 for Chinese Patent Application No. 202320502531.5, a foreign counterpart to U.S. Appl. No. 17/723,967, 2 pages.
Chinese Office Action mailed Oct. 31, 2022 for Chinese Patent Application No. 202220895988.2, a foreign counterpart to U.S. Appl. No. 17/723,967, 2 pages.
Chinese Office Action mailed Jul. 7, 2023 for Chinese Patent Application No. 202320502531.5, a foreign counterpart to U.S. Appl. No. 17/723,967, 2 pages.
Extended European Search Report mailed Sep. 22, 2022 for European Patent Application No. 22168564.7, 5 pages.

* cited by examiner

INCREASING BATTERY LIFE IN HANDHELD DEVICE

CROSS-REFERENCE TO RELATED APPLICATION

This application claims the priority of U.S. Provisional Application No. 63/176,863, which was filed on Apr. 19, 2021 and is incorporated by reference herein in its entirety.

BACKGROUND

Visual observation is a common technique for healthcare providers to determine a patient's health status. Many tools exist to assist healthcare providers with visual observations of patients. For example, an otoscope assists healthcare providers with viewing inside of a patient's ear, such as during regular health check-ups and/or to investigate ear symptoms. An ophthalmoscope assists healthcare providers with viewing inside of the fundus of a patient's eye, such as part of an eye exam and/or a routine physical exam. A dermatoscope assists healthcare providers with viewing skin lesions without the interference of skin surface reflections, which is useful in distinguishing between benign and malignant lesions on a patient's skin. These are but a few examples of tools that may assist a healthcare provider with visual observations of a patient.

Conventional tools that assist healthcare providers with visual observations, such as the ones described above, include light bulbs (or light lamps, or other types of light sources) that assist the healthcare provider in making observations. However, healthcare providers may inadvertently leave the device powered on after use. This results in unnecessary battery usage and unwanted heat generation. As such, the bulb life, battery life, device readiness, and surface temperature of the device are all negatively impacted.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference number in different figures indicates similar or identical items. The systems depicted in the accompanying figures are not to scale and components within the figures may be depicted not to scale with each other.

DETAILED DESCRIPTION

Figure 1:
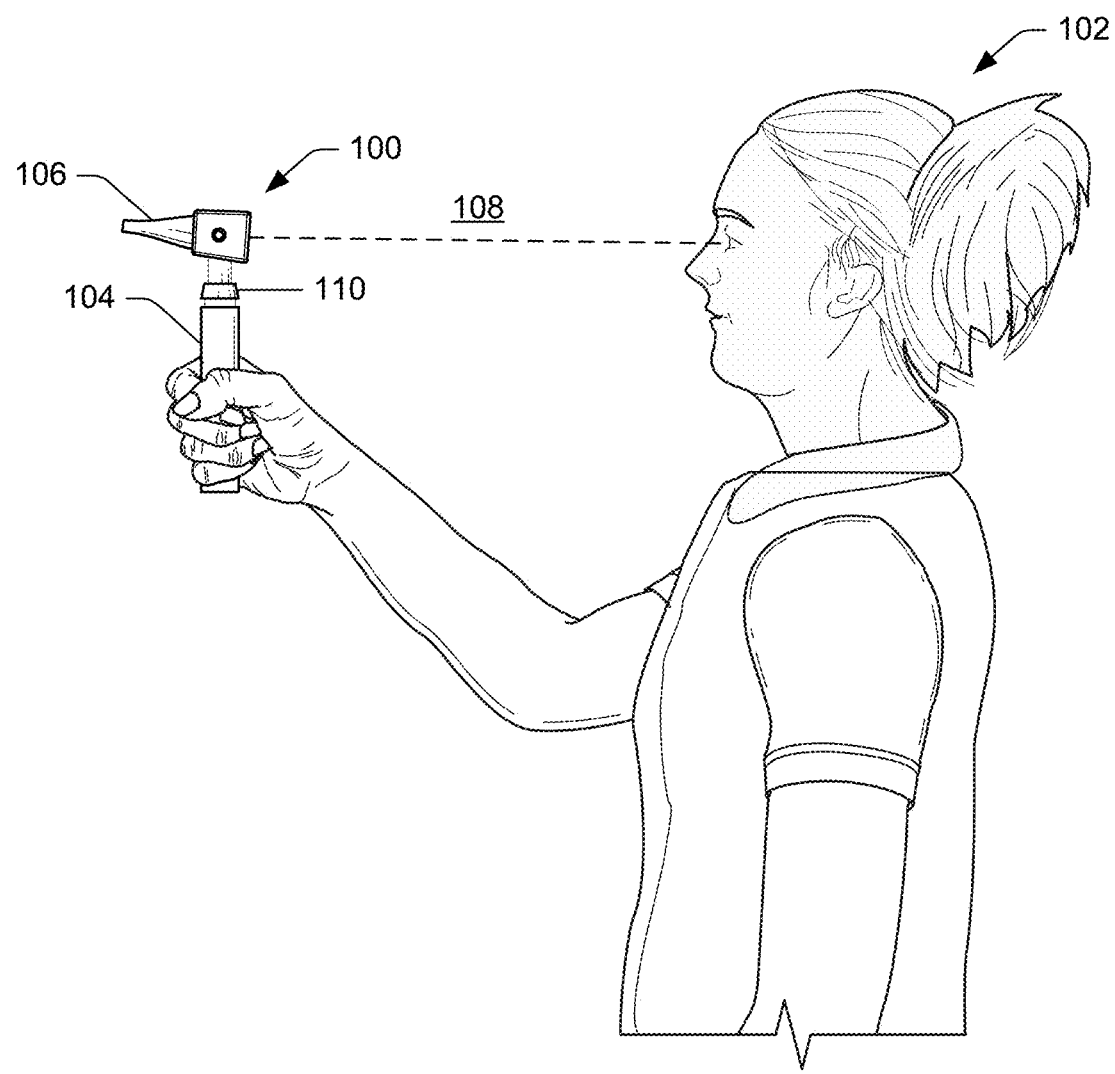
FIG. 1 illustrates an example device, according to an example of the present disclosure.

FIG. 1 illustrates an example handheld device 100 configured to enable a user 102 (e.g., healthcare provider) to perform a visual observation of another user (e.g., patient). In the illustrated example, the handheld device 100 is an otoscope configured to assist the user 102 with viewing inside of an ear, however, it is understood that the depiction of the handheld device 100 (e.g., an otoscope) is merely an example. In examples, the concepts described herein may be applicable to any other medical device that assists the user 102 with visual observations. Such devices may include, for example, probes, scopes (e.g., ophthalmoscopes, dermatoscopes, endoscopes, etc.) and the like. Additionally, while examples are generally described in relation to a handheld device, examples are considered in which the handheld device 100 assists the user 102 to perform visual observations without being held, such as worn on a head of the user 102 (e.g., a binocular ophthalmoscope), mounted to and/or placed upon a surface, and so forth.

In some instances, the handheld device 100 may include a handle 104 held in the hand of the user 102, and a head 106 coupled to the handle 104. The handle 104 may include computing components that enable an operation of the handheld device 100 (e.g., processors, memory, battery, etc.), while the head may include lenses, light sources (e.g., light bulbs), and/or other hardware to enable observation of the patient. In some instances, the head 106 may be removably coupled to the handle 104 for cleaning, replacement, and so forth. Additionally, in some instances, the head 106 may be interchangeable with other heads that couple to the handle 104. In some instances, the head 106 may include different types of light sources, such as light emitting diodes (LEDs) and/or Halogen light bulbs. As discussed herein, depending on the type of light source within the head 106, the handheld device 100 may supply varying amounts of voltages to the light source and/or may adjust other parameters associated with illuminating the light source. In some instances, the handle 104 and the head 106 may couple together using snap-fits, male/female connectors (e.g., threads), and so forth. Additionally, one or more wires and/or couplings may communicatively couple the handle 104 to the head 106 (e.g., for supplying power).

In some instances, the handheld device 100 may include a first end oriented towards (e.g., facing) the patient and the second end may be oriented towards (e.g., facing) the user 102 during an examination. In such instances, light 108 reflected by at least a portion of the patient enters the first end of the handheld device 100. Noted above, the handheld device 100 may include lenses, mirrors, beam splitters, or other light manipulating components tailored to direct the light 108 towards the user 102 and assist the user 102 with a particular type of visual observation of the patient. That is, at least a portion of the light 108 passes through the handheld device 100, along with light manipulation components included in the handheld device 100, and out of the second end of the handheld device 100 to an eye of the user 102. This enables the user 102 to make visual observations of the patient.

The handheld device 100 may include an actuator 110 (e.g., dial, lever, knob, etc.), such as a rheostatic power switch, to allow the user 102 to adjust the brightness of the light source (e.g., light bulb). For example, the user 102 may rotate the actuator 110 to increase an intensity or decrease an intensity of the light 108 emitted by the light source. In some instances, the actuator 110 may be a component of the handle 104.

Figure 2:
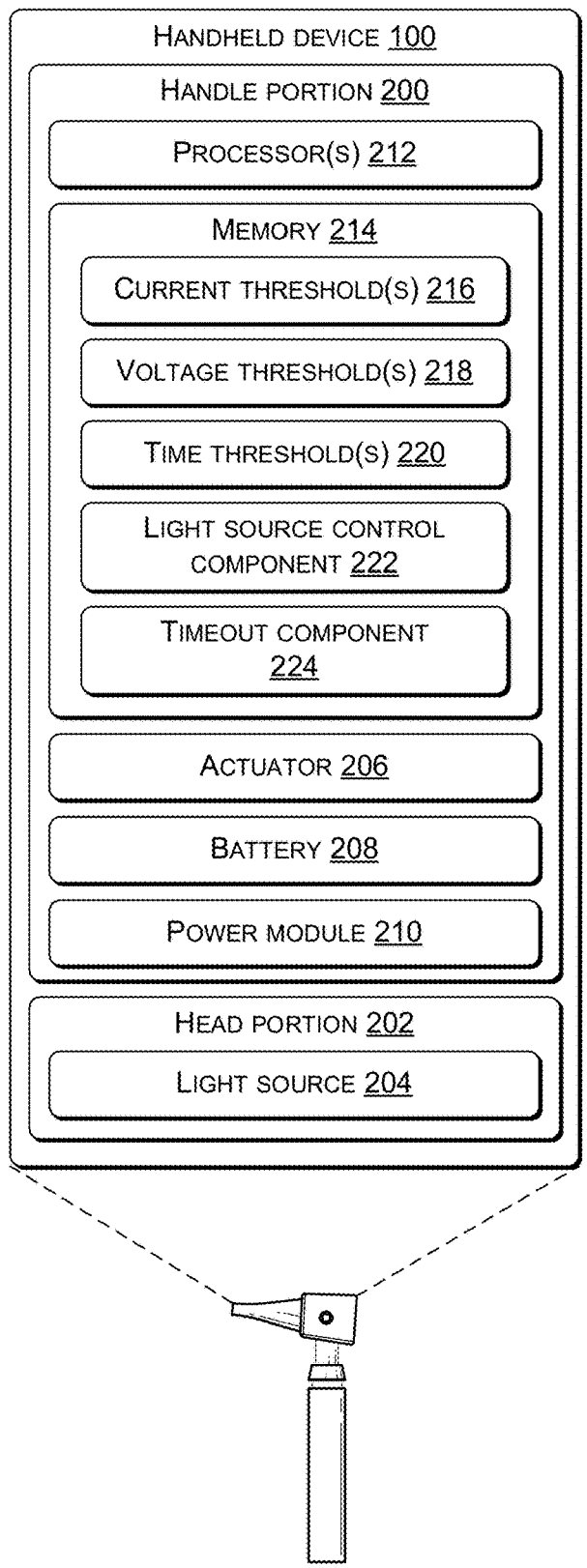
FIG. 2 illustrates example computing components of the device of FIG. 1, according to an example of the present disclosure.

FIG. 2 illustrates example computing components of the handheld device 100. The handheld device 100 is shown including a handle portion 200, which may represent the handle 104 as discussed above with regard to FIG. 1, and a head portion 202, which may represent the head 106 as discussed above with regard to FIG. 1. The handle portion 200 may be held in the hand as the user looks through the head portion 202. The head portion 202, among other components, may include a light source 204 (e.g., a light bulb) for supplying light to make visual observations of a patient, such as viewing the inside of an ear of the patient. That is, the light source 204 may be a component of the head portion 202. In some instances, the head portion 202 may be removably coupled to the handle portion 200 of the handheld device 100 (as described above with regard to FIG. 1). In this manner, different types of heads (or head portions) may be removably coupled to the handle portion 200 depending on the application, patient, and so forth. In some instances, the light source may include an LED, a Halogen light bulb, an organic LED (OLED), filaments, or any other type of light source.

The handle portion 200 includes an actuator 206, such as a dial, lever, wheel, etc. for adjusting an intensity of light emitted by the light source 204. For example, depending on the setting or desired luminosity of the light, the user may rotate, move, or otherwise actuate the actuator 206, which may adjust the intensity of the light output by the light source 204. The handle portion 200 also includes a power source, such as a battery 208, as well as a power module 210 for distributing power to components of the handle portion 200 and/or the head portion 202. In some implementations, the power source includes a capacitor in addition to or instead of the battery 208. The battery 208 may represent a rechargeable battery or a non-replaceable battery. In some instances, the battery 208 (or the power module 210) may be configured to supply varying levels of voltage to the light source 204 based on the type of head portion 202 coupled to the handle portion, or the type of light source 204 in the head portion 202.

The handle portion 200 is shown including processor(s) 212, which perform various functions and operations described herein, and memory 214 that stores instructions executable by the processor(s) 212 to perform the operations described herein. For example, the memory 214 may store or otherwise have access to current threshold(s) 216, voltage threshold(s) 218, and/or time threshold(s) 220. The current threshold(s) 216, the voltage threshold(s) 218, and/or the time threshold(s) 220 may be dependent upon the type of the light source 204 in the head portion 202. Based at least in part on the type of the light source 204, the processor(s) 212 may supply different current(s) based on the current threshold(s) 216, may supply different voltages based on the voltage threshold(s) 218, and/or may disable the light source 204 based on the time threshold(s) 220. In instances where the light source 204 includes an LED, the processor(s) 212 may supply voltages in the range of approximately between 2.0V and 5.0V. Additionally, the time threshold 220 for turning off the light source 204 and/or restricting power to the light source 204 may be ten minutes in instances where the light source 204 includes an LED.

In instances where the light source 204 includes a Halogen light bulb, the processor(s) 212 may supply voltages in the range of approximately between 1.0V and 4.0V. Additionally, the time threshold 220 for turning off the light source 204 and/or restricting power to the light source 204 may be one to five minutes (e.g., three minutes) in instances where the light source 204 includes a Halogen light bulb.

To determine the type of the light source 204, the memory 214 may store or otherwise have access to a light source control component 222. The light source control component 222 may be configured to determine an amount of current supplied to the light source 204 for use in determining the type of the light source 204. For example, the light source control component 222 may compare the amount of current to the current threshold(s) 216. If the amount of current supplied to the light source 204 is less than the current threshold 216, the light source control component 222 may determine that the light source 204 is a LED, or first type of light source. Alternatively, if the amount of current supplied to the light source 204 is greater than the current threshold 216, the light source control component 222 may determine that the light source 204 is a Halogen light bulb, or second type of light source. In some instances, the current threshold 216 may be approximately 1.0 A. Using the type of the light source 204, as noted above, the light source 204 may be supplied with a certain range of voltages. The light source control component 222 may, in some instances, control the amount of voltage supplied to the light source 204.

The memory 214 is further shown including or having access to a timeout component 224. The timeout component 224 may determine an amount of time the light source 204 is illuminated for purposes of disabling the light source 204 (e.g., turning off, restricting power, etc.) to conserve battery power, reduce a touch temperature of the handheld device 100, and/or to increase a longevity of the light source 204. For example, the timeout component 224 may determine an amount of time at which the light source 204 is illuminated, without adjustment via the actuator 206. Alternatively, the timeout component 224 may determine an amount of time a current amount of voltage is supplied to the light source 204. In some instances, the timeout component 224 may compare the amount of time at which the light source 204 has been illuminated to the time threshold(s) 220, as discussed above. For example, if the time threshold 220 has elapsed without adjustment, the timeout component 224 may determine to disable the light source 204. In response, the processor(s) 212 may restrict power to the light source 204 (e.g., via the power module 210). In some instances, the timeout component 224 may include a timer to determine the amount of time the light source 204 has been illuminated and/or an amount of time light source 204 has been illuminated without adjustment.

As used herein, a processor, such as processor(s) 212 may include multiple processors and/or a processor having multiple cores. Further, the processor(s) may include one or more cores of different types. For example, the processor(s) may include application processor units, graphic processing units, and so forth. In one implementation, the processor(s) may include a microcontroller and/or a microprocessor. The processor(s) may include a graphics processing unit (GPU), a microprocessor, a digital signal processor or other processing units or components known in the art. Alternatively, or in addition, the functionally described herein can be performed, at least in part, by one or more hardware logic components. For example, and without limitation, illustrative types of hardware logic components that may be used include field-programmable gate arrays (FPGAs), application-specific integrated circuits (ASICs), application-specific standard products (ASSPs), system-on-a-chip systems (SOC s), complex programmable logic devices (CPLDs), etc. Additionally, each of the processor(s) may possess its own local memory, which also may store program components, program data, and/or one or more operating systems.

The memory 214 may include volatile and nonvolatile memory, removable and non-removable media implemented in any method or technology for storage of information, such as computer-readable instructions, data structures, program component, or other data. Such memory may include, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory may be implemented as computer-readable storage media ("CRSM"), which may be any available physical media accessible by the processor(s) 212 to execute instructions stored on the memory. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processor(s) 212.

Figure 3:
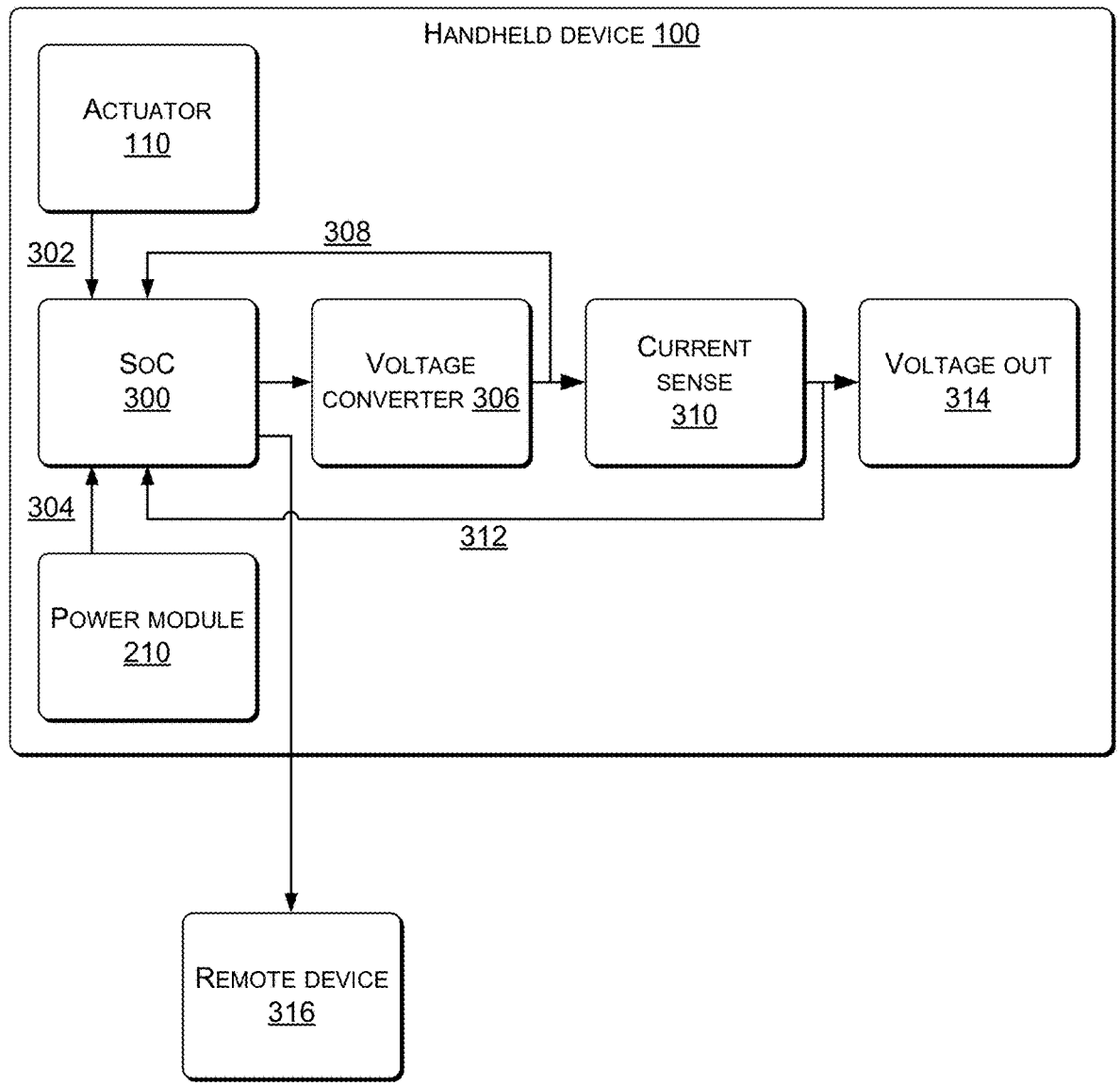
FIG. 3 illustrates additional example computing components of the device of FIG. 1, according to an example of the present disclosure.

FIG. 3 illustrates additional example computing components of the handheld device 100. The handheld device 100 may include a system on a chip (SoC) 300 configured to receive, or measure, voltages supplied to various components of the handheld device 100. The SoC 300 may represent an analog-to-digital converter for determining the amount of voltages supplied to the various components.

The SoC 300 may receive a first voltage reading 302 from the actuator 110 associated with an intensity of light to be supplied by the handheld device 100 to the light source 204. The SoC 300 may also receive a second voltage reading 304 from the power module 210 associated with a battery charge of the battery 208. The SoC 300 may communicate with a voltage converter 306 (e.g., using I2C) to enable the light source 204 or disable the light source 204.

The voltage converter 306 represents an electric power converter which changes the voltage supplied by the battery 208. For example, depending on the type of the light source 204 coupled to the handle portion 200, the voltage converter 306 may supply a respective amount of voltage. In some instances, the amount of voltage, or the amount of change in the voltage by the voltage converter 306 may be dependent upon the voltage threshold(s) 218 as discussed above. A third voltage 308 may be received by the SoC 300 that represents a current sense reference of the voltage converter 306.

A current sense 310 may represent an amplifier that outputs a voltage proportional to the current being supplied. In some instances, the current sense 310 may include a 1.0 Ohm resistor. The SoC 300 may receive a fourth voltage reading 312 that represents a current sense. Finally, a voltage may be output to the head portion 202 at 314.

In some instances, a remote device 316 may be communicatively coupled to the handheld device 100 for debugging errors experienced by the handheld device 100. For example, the remote device 316 may monitor voltages received by the SoC 300 to determine whether the voltages are sporadic, outside ranges, and so forth.

Figure 4:
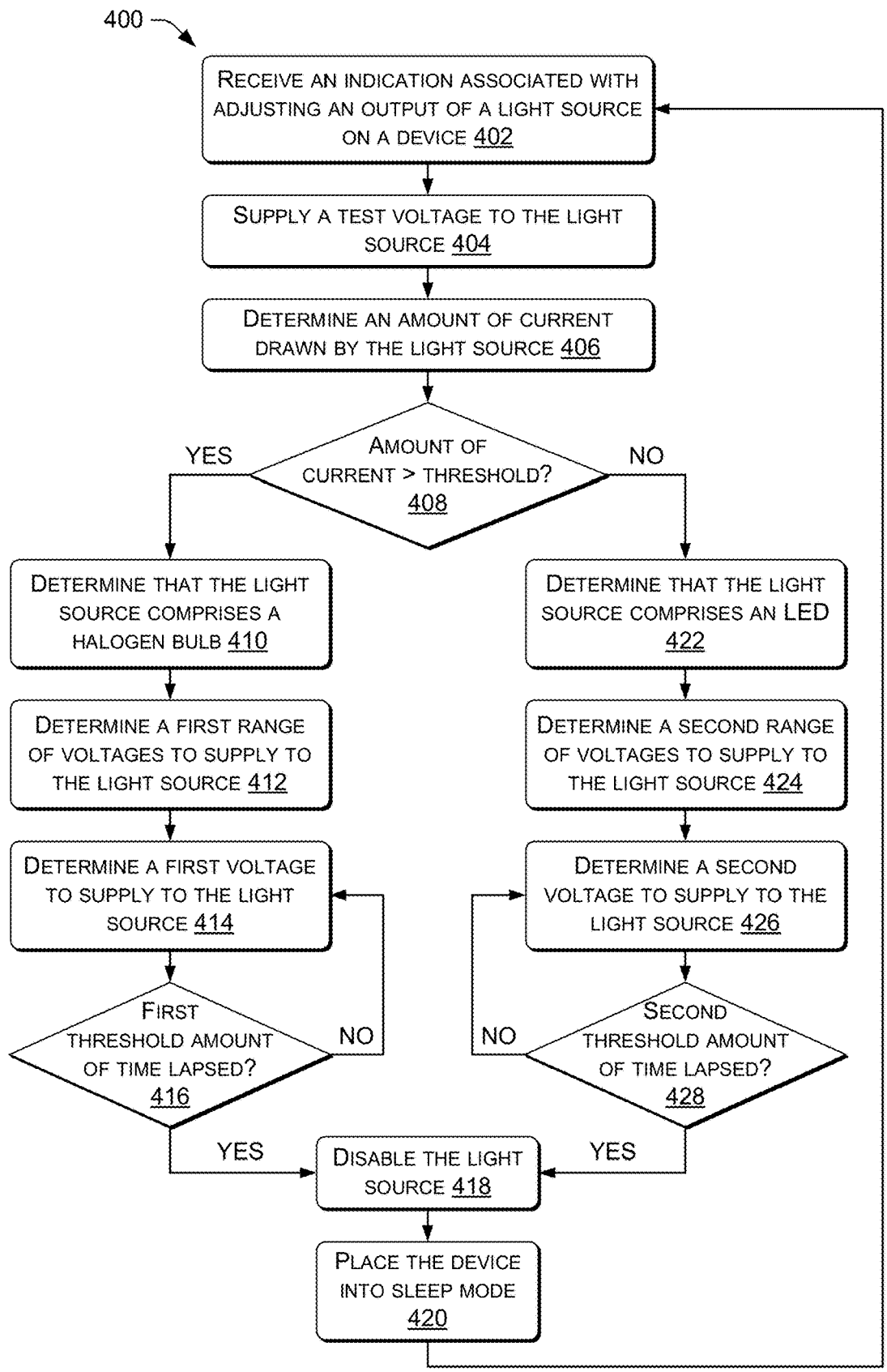
FIG. 4 illustrates an example process for determining a type of light source for use in adjusting one or more setting(s) of the device, according to an example of the present disclosure.
Figure 5:
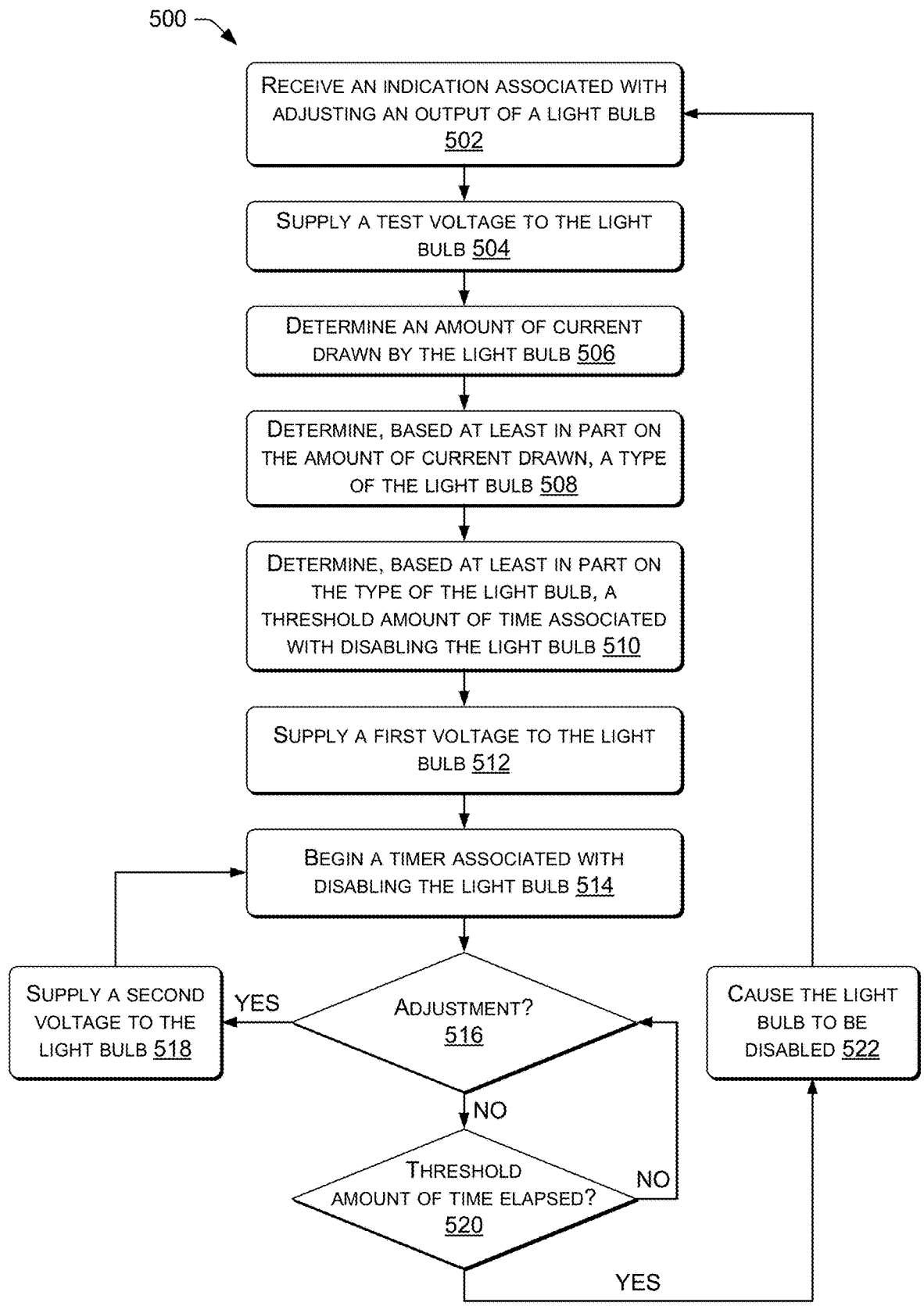
FIG. 5 illustrates an example process for determining a type of light source for use in adjusting one or more setting(s) of the device, according to an example of the present disclosure.

FIGS. 4 and 5 illustrate various processes related controlling an operation of a device, such as the handheld device 100, based on a type of detected light source. The processes described herein are illustrated as collections of blocks in logical flow diagrams, which represent a sequence of operations, some or all of which may be implemented in hardware, software, or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1-3, although the processes may be implemented in a wide variety of other environments, architectures and systems.

FIG. 4 illustrates an example process 400 for determining a type of light source within a device, such as an ophthalmoscope or an otoscope, for use in determining an amount of time associated with disabling the device. In some instances, the process 400 may be performed, at least in part, by the handheld device 100.

At 402, the process 400 may include receiving or otherwise identifying an indication associated with adjusting an output of a light source on a device. For example, an user may adjust an actuator, such as a rheostat (e.g., dial, lever, switch, etc.) to adjust an intensity of the light source of the device. The indication may be representative of a position of the actuator 110. By way of illustration, during an examination, the user may maneuver the actuator to either turn on the device, adjust an intensity (e.g., brightness) of the device, and so forth. In some instances, the adjustment may include a movement of the actuator from a first position (e.g., initial position, initial intensity, etc.) to a second position (e.g., subsequent position, subsequent intensity, etc.).

At 404, the process 400 may include supplying a test voltage to the light source. For example, based at least in part on receiving the indication to adjust the output of the light source, the device may supply the test voltage to the light source. In some instances, the test voltage may be in the range of approximately 1.5V to approximately 3.0V.

At 406, the process 400 may include determining an amount of current drawn by the light source. For example, supplying the test voltage may be used, at least in part, to determine the type of light source connected (or included within) the device. For example, based on the type of light source (e.g., Halogen, LED, etc.), the light source may draw different amounts of power. As such, by supplying the test voltage, the device may determine the type of light source coupled to the device. In some instance, the amount of current drawn by the light source may be in the range of approximately 0.5 A to approximately 1.5 A.

At 408, the process 400 may include determining whether the amount of current is greater than a threshold. For example, the device may compare the amount of current drawn by the light source to a threshold. Noted above, the threshold may be established (or determined) to indicate whether the light source coupled to the device is a Halogen or LED. If the light source includes a Halogen light bulb, then the light source will draw a greater amount of amps, compared to if the light source includes a LED. In some instances, the Halogen light bulb may draw greater than 1.0 A, whereas a LED may draw less than 1.0 A. As such, in some instances, the threshold at 408 may be 1.0 A.

If at 408, the process 400 determines that the amount of current is greater than the threshold, the process 408 may follow the "YES" route and proceed to 410. At 410, the process 400 may determine that the light source includes a Halogen light bulb. That is, if the amount of current being drawn by the light source is greater than the threshold (e.g., 1.25 A), the device may determine that the device is coupled to a Halogen light bulb.

At 412, the process 400 may include determining a first range of voltages to supply to the light source. For example, based at least in part on the device being coupled to the Halogen light bulb, the device may determine a first range of voltages to be supplied to the light source. In this sense, the device may supply respective voltages to the Halogen light bulb to vary a range of intensity emitted. In some instances, the first range of voltages for the Halogen light bulb may be between approximately 1.0V and 4.0V.

At 414, the process 400 may include determining a first voltage to supply to the light source. For example, the device may determine a first voltage to supply to light source. In some instances, the amount of voltage to be supplied to the light source may be based on the indication received at 402, or a position of the actuator of the device. In other words, after determining the type of light source coupled to the device, the device may determine a respective voltage to supply to the light source and according to the adjustment made by the user.

At 416, the process 400 may include determining whether a first amount of time has elapsed since supplying the first voltage. For example, based at least in part on supplying the first voltage to the light source, the device may begin a timer. The timer may be associated with how long the device supplies the first voltage to the light source, or how long the device has supplied the first voltage to the light source. In some instances, the timer may begin a countdown associated with disabling the light source (e.g., power down) to avoid draining a battery life of the device. In other words, if the device supplies the first voltage for the threshold amount of time, and without adjustments made by the user (e.g., an adjustment to the actuator), the device may determine that the device is no longer being used. Alternatively, if the user makes an adjustment to the actuator, so as to increase an intensity of the light source or decrease an intensity of the light source, the device may reset the timer and begin a new countdown for disabling the light source. In some instances, the first threshold amount of time may be approximately one minute, two minutes, three minutes, or four minutes.

If at 416, the device determines that the first threshold amount of time has not lapsed since supplying the first voltage, or that an adjustment to the device has been made, the process 400 may follow the "NO" route and loop to 414 to continue to supply the first voltage (or a new voltage associated with an adjustment to the device) and for determining whether the first threshold amount of time has elapsed. As such, the device may supply the first voltage (or the new voltage associated with an adjustment to the device) until the first threshold amount of time has elapsed.

Alternatively, if at 416 the device determines that the first threshold amount of time has elapsed, the process 400 may follow the "YES" route and proceed to 418. At 418, the process 400 may include disabling the light source. For example, based at least in part on the first threshold amount time elapsing, the device may disable the light source by restricting power to the light source. Disabling the light source may increase a battery life of the battery, reduce a touch temperature of the device, and increase a longevity of the light source.

At 420, the process 400 may include placing the device into a sleep mode. For example, the device may supply minimal power to processors, modules, or other components of the device. In some instances, in the sleep mode, the device may supply minimal power to conserve the battery. For example, the device may continue to supply a minimum amount of voltage to processors to detect a change in the actuator when the user desires to power up the device or otherwise use the device. As such, by selectively supplying power to components of the device, the device may conserve a battery life of the battery but may be permitted to detect adjustments in the device for powering up the device. For example, from 420, the process 400 may loop to 402 for detecting an adjustment of the device.

If at 422, the process 400 determines that the amount of current is not greater than the threshold amount of current, the process 400 may follow the "NO" route and proceed to 422. At 422, the process 400 may determine that the light source includes a LED. That is, if the amount of current being drawn by the light source is less than the threshold (e.g., 0.075 A), the device may determine that the device is coupled to a LED.

At 424, the process 400 may include determining a second range of voltages to supply to the light source. For example, based at least in part on the device being coupled to the LED, the device may determine a second range of voltages to be supplied to the light source. In this sense, the device may supply respective voltages to the LED to vary a range of intensity emitted by the light source. In some instances, the second range of voltages for the LED may be between approximately 2.0V and 5.0V.

At 426, the process 400 may include determining a second voltage to supply to the light source. For example, the device may determine a second voltage to supply to the light source. In some instances, the amount of voltage to be supplied to the light source may be based on the indication received at 402, or a position of the actuator. In other words, after determining the type of light source coupled to the device, the device may determine a respective voltage to supply to the light source and according to the adjustment made by the user.

At 428, the process 400 may include determining whether a second amount of time has elapsed since supplying the second voltage. For example, based at least in part on supplying the second voltage to the light source, the device may begin a timer. The timer may be associated with how long the device supplies the second voltage to the light source, or how long the device has supplied the second voltage to the light source. In some instances, the timer may begin a countdown associated with disabling the light source (e.g., power down) to avoid draining the battery and/or to reduce a touch temperature of the device. In other words, if the device supplies the second voltage for the second threshold amount of time, and without any adjustments made by the user (e.g., an adjustment to rheostat), the device may determine that the device is no longer being used. Alternatively, if the user makes an adjustment to the actuator, the device may reset the timer and begin a new countdown for disabling the light source. In some instances, the second threshold amount of time may be approximately five minutes, seven minutes, nine minutes, or ten minutes.

If at 428, the device determines that the second threshold amount of time has not lapsed since supplying the second voltage, or that an adjustment to the device has been made, the process 400 may follow the "NO" route and loop to 426 to continue to supply the second voltage (or a new voltage associated with an adjustment to the device) and for determining whether the second threshold amount of time has elapsed. As such, the device may supply the second voltage (or the new voltage associated with an adjustment to the device) until the second threshold amount of time has elapsed. Alternatively, if at 428 the device determines that the second threshold amount of time has elapsed, the process 400 may follow the "YES" route and proceed to 418 to disable the light source and then to 420 to place the device into sleep mode.

FIG. 5 illustrates an example process 500 for determining an amount of time associated with disabling a light source coupled to a device, based at least in part on a type of the light source coupled to the device. In some instances, the process 500 may be performed, at least in part, by the handheld device 100.

At 502, the process 500 may include receiving an indication associated with adjusting an output of a light source on a device. For example, an user may adjust an actuator of the device to adjust an intensity of the light source of the device. By way of illustration, during an examination, the user may maneuver the actuator to either turn on the device, adjust an intensity (e.g., brightness) of the device, and so forth. In some instances, the adjustment may include a movement of the actuator from a first position (e.g., initial position, initial intensity, etc.) to a second position (e.g., subsequent position, subsequent intensity, etc.).

At 504, the process 500 may include supplying a test voltage to the light source. For example, based at least in part on receiving the indication to adjust the output of the light source, the device may supply the test voltage to the light source. In some instances, the test voltage may be in the range of approximately 1.5V to approximately 3.0V.

At 506, the process 500 may include determining an amount of current drawn by the light source. For example, supplying the test voltage may be used, at least in part, to determine the type of light source connected (or included within) the device. For example, based on the type of light source (e.g., Halogen, LED, etc.), the light source may draw a respective amount of power. As such, by supplying the test voltage, the device may determine the type of light source coupled to the device. In some instances, the amount of current drawn by the light source may be in the range of approximately 0.5 A to approximately 1.5 A.

Accordingly, at 508, the process 500 may include determining, based at least in part on the amount of current drawn, a type of the light source. In some instances, the device may determine the type of light source based on comparing the amount of current drawn to a threshold. For example, comparison of the amount of current to a threshold amount of current may indicate whether the light source is a LED or a Halogen light bulb. In some instances, if the amount of current is greater than the threshold amount of current (e.g., 1.0 A), the device may determine that the light source includes a Halogen light bulb.

At 510, the process 500 may include determining, based at least in part on the type of light source, a threshold amount of time associated with disabling the light source. For example, the device may determine a threshold amount of time associated with powering off the light source after the threshold amount of time in which the device has not been used to conserve a battery life of the device and/or to reduce a touch temperature of the device. In some instances, if the light source includes an LED, the threshold amount of time may be approximately ten minutes, whereas if the light source includes a Halogen light bulb, the threshold amount of time may be approximately 3 minutes. As such, based at least in part on the type of the light source, the device may determine a respective amount of time associated with disabling the light source.

At 512, the process 500 may include supplying a first voltage to the light source. For example, based at least in part on the adjustment of the output of the device at 502, the device may determine the first voltage to supply to the light source. As such, based on the position of the actuator, the intensity of the light source may be adjusted.

At 514, the process 500 may include beginning a timer associated with disabling the light source. For example, based at least in part on the device supplying the first voltage to the light source, the device may begin a timer. The timer may represent an amount of time (i.e., how long) the device has supplied the first voltage to the light source.

At 516, the process 500 may determine whether an adjustment has been made to the device. For example, the device may determine whether the user has adjusted a position of the actuator to increase or decrease an intensity of light emitted by the light source. The adjustment of the device may accordingly vary an amount of voltage supplied to the light source to either increase or decrease the intensity of light. If at 516 the process 500 determines that an adjustment has been made, the process 500 may follow the "YES" route and proceed to 518.

At 518, the process 500 may include supplying a second voltage to the light source. For example, the device may supply the second voltage to the light source. The second voltage may be based at least in part the adjustment to the device. That is, the second voltage supplied to the light source may be according to the adjustment to either increase or decrease an intensity of the light source. From 518, the process 500 may proceed to 514 whereby the process 500 may begin the timer. As such, in instances where an adjustment is made, the device may reset the timer or begin a new timer to determine an amount of time (i.e., how long), the device has supplied the second voltage to the light source. Therein, the process 500 may proceed to 516 to determine whether other adjustments are made. If so, the process 500 may supply a new, or different, amount of voltage and begin a new timer for disabling the light source.

If at 516, the process 500 determines that the adjustment has not been made to the device, the process 500 may follow the "NO" route and proceed to 520. At 520, the process 500 may determine whether the threshold amount of time has elapsed. For example, the device may compare an amount of time associated with the device supplying the first voltage (second voltage, or other voltage) to the light source for the threshold amount of time. This may, in some instances, involve determining when the timer began at 514. If at 516 the process 500 determines that the threshold amount of time has not elapsed, the process 500 may follow the "NO" route and loop to 516 to determine whether any adjustments are made, and for determining whether the threshold amount of time has elapsed. Alternatively, if at 516 the process 500 determines that the threshold amount of time has elapsed, the process 500 may follow the "YES" route and proceed to 518.

At 518, the process 500 may include disabling the light source. For example, based at least in part on the threshold amount time elapsing, the device may disable the light source by restricting power to the light source. Disabling the light source may increase a battery life of the battery, reduce a touch temperature of the device, and increase a longevity of the light source.

EXAMPLE CLAUSES

1. A medical device, including: a head including a light scope; and a handle coupled to the head portion, the handle portion including: a battery configured to supply a voltage to the light scope; one or more processors; and memory storing instructions that, when executed by the one or more processors, cause the one or more processors to perform acts including: receiving an indication associated with adjusting an output of the light scope; determining an amount of current drawn by the light scope from the battery; determining, based at least in part on the amount of current drawn, that the light scope includes a Halogen light scope or a light emitting diode (LED); determining, based at least in part on determining that the light scope includes the Halogen light scope or the LED, a threshold amount of time; determining that the threshold amount of time has elapsed since the battery has supplied the voltage to the light scope; and causing, based at least in part on the threshold amount of time elapsing, the light scope to be disabled by disconnecting the battery from the light scope.

2. The medical device of clause 1, wherein determining, based at least in part on the amount of current drawn, that the light scope includes the Halogen light scope or the LED includes comparing the current drawn to a threshold current.

3. The medical device of clause 1 or 2, wherein the medical device includes at least one of an ophthalmoscope, a dermatoscope, an endoscope, or a probe.

4. A medical device, including: a head portion including a light scope; and a handle portion coupled to the head portion, the handle portion including: one or more processors; one or more non-transitory computer-readable media storing computer-executable instructions that, when executed by the one or more processors, cause the one or more processors to perform acts including: receiving an indication associated with adjusting an output of the light scope; determining an amount of current drawn by the light scope; determining, based at least in part on the amount of current drawn, a type of the light scope; determining, based at least in part on the type of the light scope, an amount of time associated with disabling the light scope; and causing a voltage to be supplied to the light scope.

5. The medical device of clause 4, the acts further including: determining a time associated with causing the voltage to be supplied to the light scope; determining that the voltage has been supplied to the light scope for a threshold amount of time; and terminating supply of the voltage the light scope.

6. The medical device of clause 5, the acts further including determining, based at least in part on the type of the light scope, the threshold amount of time.

7. The medical device of one of clauses 4 to 6, the acts further including: determining that the amount of current drawn by the light scope is greater than a threshold amount of current, wherein the type of the light scope includes a Halogen light scope, or determining that the amount of current drawn by the light scope is less than a threshold amount of current, wherein the type of the light scope includes a light emitting diode (LED) light scope.

8. The medical device of one of clauses 4 to 7, wherein handle further includes a power source configured to supply the voltage to the light scope.

9. The medical device of one of clauses 4 to 7, wherein the medical device includes at least one of an ophthalmoscope, a dermatoscope, an endoscope, or a probe.

10. A method, including: determining an amount of current being drawn by a light scope; determining, based at least in part on the amount of current, a type of light scope associated with the light scope; determining, based at least in part on the type of light scope, a threshold amount of time associated with disabling the light scope; and causing a voltage to be supplied to the light scope.

11. The method of clause 10, further including: determining that the threshold amount of time has elapsed since supplying the voltage; and causing, based at least in part on the threshold amount of time elapsing, the light scope to be disabled by terminating power to the light scope.

12. The method of clause 10 or 11, further including: receiving an indication associated with one of an output of the light scope or of an output of a second light scope; determining a second amount of current being drawn by one of the light scope or the second light scope; and determining, based at least in part on the second amount of current, that the light scope includes the type of light scope or a second type of light scope.

13. The method of one of clauses 10 to 12, further including: receiving an indication associated with an adjustment to the voltage; causing a second voltage to be supplied to the light scope; determining that the threshold amount of time has elapsed since supplying the second voltage; and causing, based at least in part on the threshold amount of time elapsing, the light scope to be disabled by terminating power to the light scope.

14. The method of one of clauses 10 to 13, further including determining, based at least in part on the type of light scope, a range of voltages to supply the light scope, the voltage being within the range of voltages.

15. The method of one of clauses 10 to 14, further including determining that the amount of current is greater than a threshold amount of current, wherein determining the type of light scope includes determining that the light scope includes a Halogen light scope.

16. The method of one of clauses 10 to 15, further including determining that the amount of current is less than a threshold amount of current, wherein determining the type of light scope includes determining that the light scope includes a light emitting diode (LED) light scope.

17. The method of one of clauses 10 to 16, further including: determining that the threshold amount of time has not elapsed since supplying the voltage; and causing the voltage to be supplied to the light scope.

18. The method of one of clauses 10 to 17, further including causing a test voltage to be supplied to the light scope, and wherein determining the amount of current being drawn by the light scope is based at least in part on the test voltage.

19. The method of one of clauses 10 to 18, further including: determining an absence of an adjustment to the voltage supplied to the light scope; determining that the threshold amount of time has elapsed since supplying the voltage; and causing the light scope to be disabled by terminating power to the light scope.

20. The method of one of clauses 10 to 19, wherein the method is performed by at least one of an ophthalmoscope, an otoscope, a dermatoscope, an endoscope, or a probe.

21. A device including a processor configured to perform the method of one of clauses 10 to 20.

22. A scope configured to perform the method of one of clauses 10 to 20.

23. One or more non-transitory computer readable media storing instructions executable by a processor, wherein the instructions, when executed, cause the processor to perform operations including the method of one of clauses 10 to 20.

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A medical device, comprising:
a head comprising a light source; and
a handle coupled to the head, the handle comprising:
   a battery configured to supply a voltage to the light source;
   one or more processors; and
   memory storing instructions that, when executed by the one or more processors, cause the one or more processors to perform acts comprising:
      receiving an indication associated with adjusting an output of the light source; determining an amount of current drawn by the light source from the battery;
      determining, based at least in part on the amount of current drawn, that the light source comprises a Halogen light bulb or a light emitting diode (LED);
      determining, based at least in part on determining that the light source comprises the Halogen light bulb or the LED, a threshold amount of time;
      determining that the threshold amount of time has elapsed since the battery has supplied the voltage to the light source; and
      causing, based at least in part on the threshold amount of time elapsing, the light source to be disabled by disconnecting the battery from the light source.

2. The medical device of claim 1, wherein determining, based at least in part on the amount of current drawn, that the light source comprises the Halogen light bulb or the LED comprises comparing the current drawn to a threshold current.

3. The medical device of claim 1, wherein the medical device comprises at least one of an ophthalmoscope, an otoscope, a dermatoscope, an endoscope, or a probe.

4. A medical device, comprising:
a head portion including a light source; and
a handle portion coupled to the head portion, the handle portion including:
   one or more processors;
   one or more non-transitory computer-readable media storing computer-executable instructions that, when executed by the one or more processors, cause the one or more processors to perform acts comprising:
      receiving an indication associated with adjusting an output of the light source;
      determining an amount of current drawn by the light source;
      determining, based at least in part on the amount of current drawn, a type of the light source;
      determining, based at least in part on the type of the light source, an amount of time associated with disabling the light source;
      causing a voltage to be supplied to the light source;
      determining a time associated with causing the voltage to be supplied to the light source;
      determining that the voltage has been supplied to the light source for a threshold amount of time; and
      terminating supply of the voltage to the light source.

5. The medical device of claim 4, the acts further comprising determining, based at least in part on the type of the light source, the threshold amount of time.

6. The medical device of claim 4, the acts further comprising:
   determining that the amount of current drawn by the light source is greater than a first threshold amount of current, wherein the type of the light source comprises a Halogen light bulb, or
   determining that the amount of current drawn by the light source is less than a second threshold amount of current, wherein the type of the light source comprises a light emitting diode (LED).

7. The medical device of claim 4, wherein handle further comprises a power source configured to supply the voltage to the light source.

8. The medical device of claim 4, wherein the medical device comprises at least one of an ophthalmoscope, a dermatoscope, an endoscope, or a probe.

9. A method, comprising:
providing the medical device of claim 4;
determining an amount of current being drawn by the light source;
determining, based at least in part on the amount of current, a type of the light source;
determining, based at least in part on the type of light source, an amount of time associated with disabling the light source;
causing a voltage to be supplied to the light source;
determining a length of time associated with causing the voltage to be supplied to the light source;
determining, based on the length of time, that the voltage has been supplied to the light source for a threshold amount of time; and
terminating supply of the voltage to the light source.

10. The method of claim 9, further comprising:
receiving an indication associated with one of an output of the light source or of an output of a second light source;
determining a second amount of current being drawn by one of the light source or the second light source; and
determining, based at least in part on the second amount of current, that the light source comprises the type of light source or a second type of light source.

11. The method of claim 9, further comprising:
receiving an indication associated with an adjustment to the voltage;
causing a second voltage to be supplied to the light source;
determining that the threshold amount of time has elapsed since supplying the second voltage; and
causing, based at least in part on the threshold amount of time elapsing, the light source to be disabled by terminating power to the light source.

12. The method of claim 9, further comprising determining, based at least in part on the type of light source, a range of voltages to supply the light source, the voltage being within the range of voltages.

13. The method of claim 9, further comprising determining that the amount of current is greater than a threshold amount of current, wherein determining the type of light source comprises determining that the light source comprises a Halogen light bulb.

14. The method of claim 9, further comprising determining that the amount of current is less than a threshold amount of current, wherein determining the type of light source comprises determining that the light source comprises a light emitting diode (LED).

15. The method of claim 9, further comprising:
determining that the threshold amount of time has not elapsed since supplying the voltage; and
upon determining that the threshold amount of time has not elapsed since supplying the voltage, continuing to cause the voltage to be supplied to the light source.

16. The method of claim 9, further comprising causing a test voltage to be supplied to the light source, and wherein determining the amount of current being drawn by the light source is based at least in part on the test voltage.

17. The method of claim 9, further comprising:
determining an absence of an adjustment to the voltage supplied to the light source;
determining that the threshold amount of time has elapsed since supplying the voltage; and
causing the light source to be disabled by terminating power to the light source.

18. The method of claim 9, wherein the method is performed by at least one of an ophthalmoscope, an otoscope, a dermatoscope, an endoscope, or a probe.

* * * * *